US012591922B2

(12) United States Patent
Fujii

(10) Patent No.: US 12,591,922 B2
(45) Date of Patent: Mar. 31, 2026

(54) SYSTEM, METHOD, AND PROGRAM FOR DETERMINING COMMODITY OR SERVICE SUITABLE FOR USER

(71) Applicant: ADVASA Co., Ltd., Tokyo (JP)

(72) Inventor: Hideki Fujii, Tokyo (JP)

(73) Assignee: ADVASA Co., Ltd., Tokyo (JP)

( * ) Notice: Subject to any disclaimer, the term of this patent is extended or adjusted under 35 U.S.C. 154(b) by 290 days.

(21) Appl. No.: 18/549,820

(22) PCT Filed: Mar. 8, 2022

(86) PCT No.: PCT/JP2022/010100
§ 371 (c)(1),
(2) Date: Mar. 27, 2024

(87) PCT Pub. No.: WO2022/191210
PCT Pub. Date: Sep. 15, 2022

(65) Prior Publication Data
US 2024/0242262 A1 Jul. 18, 2024

(30) Foreign Application Priority Data
Mar. 9, 2021 (JP) ................................. 2021-037562

(51) Int. Cl.
*G06Q 30/00* (2023.01)
*G06Q 30/0601* (2023.01)
(Continued)

(52) U.S. Cl.
CPC ......... *G06Q 30/0631* (2013.01); *G06Q 40/08* (2013.01); *G16H 50/30* (2018.01)

(58) Field of Classification Search
CPC ................................................. G06Q 30/06–08
See application file for complete search history.

(56) References Cited

U.S. PATENT DOCUMENTS 10,504,385 B1 * 12/2019 Harris .................... G09B 5/125
2006/0190347 A1 * 8/2006 Cuervo ............. G06Q 30/0601
705/26.1
(Continued)

FOREIGN PATENT DOCUMENTS

| JP | 2008198163 A | 8/2008 |
|----|--------------|--------|
| JP | 2019109620 A | 7/2019 |
| JP | 6816905 B1 | 1/2021 |

OTHER PUBLICATIONS

International Search Report for related International Application No. PCT/JP2022/010100 mailed May 17, 2022 and its English Translation.
(Continued)

*Primary Examiner* — Ethan D Civan
(74) *Attorney, Agent, or Firm* — Renner, Otto, Boisselle & Sklar, LLP

(57) ABSTRACT
The present invention provides a system for determining a commodity or service suitable for a user. The system is configured to perform: acquisition of data and/or information regarding the user (step S701); calculation of a score that multi-dimensionally represents a feature of the user on the basis of the acquired data and/or information regarding the user (step S702); and determination of a commodity or service suitable for the user, by using the score (step S703).

15 Claims, 9 Drawing Sheets

700

(51) Int. Cl.
G06Q 40/08       (2012.01)
G16H 50/30       (2018.01)

(56) References Cited

U.S. PATENT DOCUMENTS

| | | | |
|---|---|---|---|
| 2013/0054281 A1* | 2/2013 | Thakkar ............. | G06Q 30/0207 |
| | | | 705/5 |
| 2016/0086250 A1* | 3/2016 | Gunjan ............. | G06Q 30/0631 |
| | | | 705/26.7 |
| 2018/0130548 A1* | 5/2018 | Fisher ................ | G06Q 20/3227 |
| 2018/0374139 A1* | 12/2018 | Shrivastava ....... | G06Q 30/0631 |
| 2022/0197914 A1* | 6/2022 | Sodhi ................ | G06Q 30/0201 |

OTHER PUBLICATIONS

First Office Action for corresponding Japanese Application No. 2021-037562 mailed Jun. 18, 2022 and its English Machine Translation.

* cited by examiner

[FIG.1]
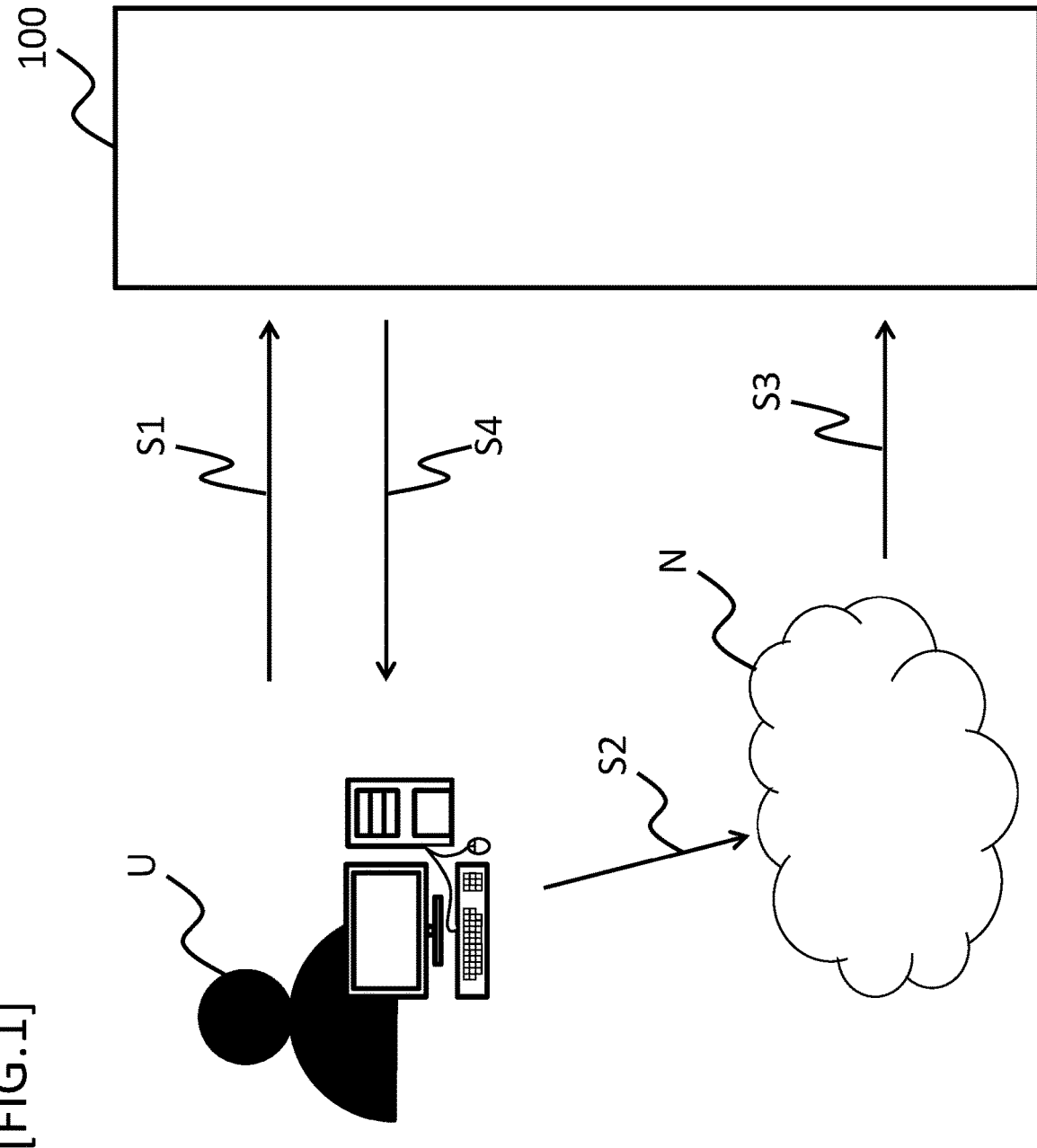

[FIG.2A]
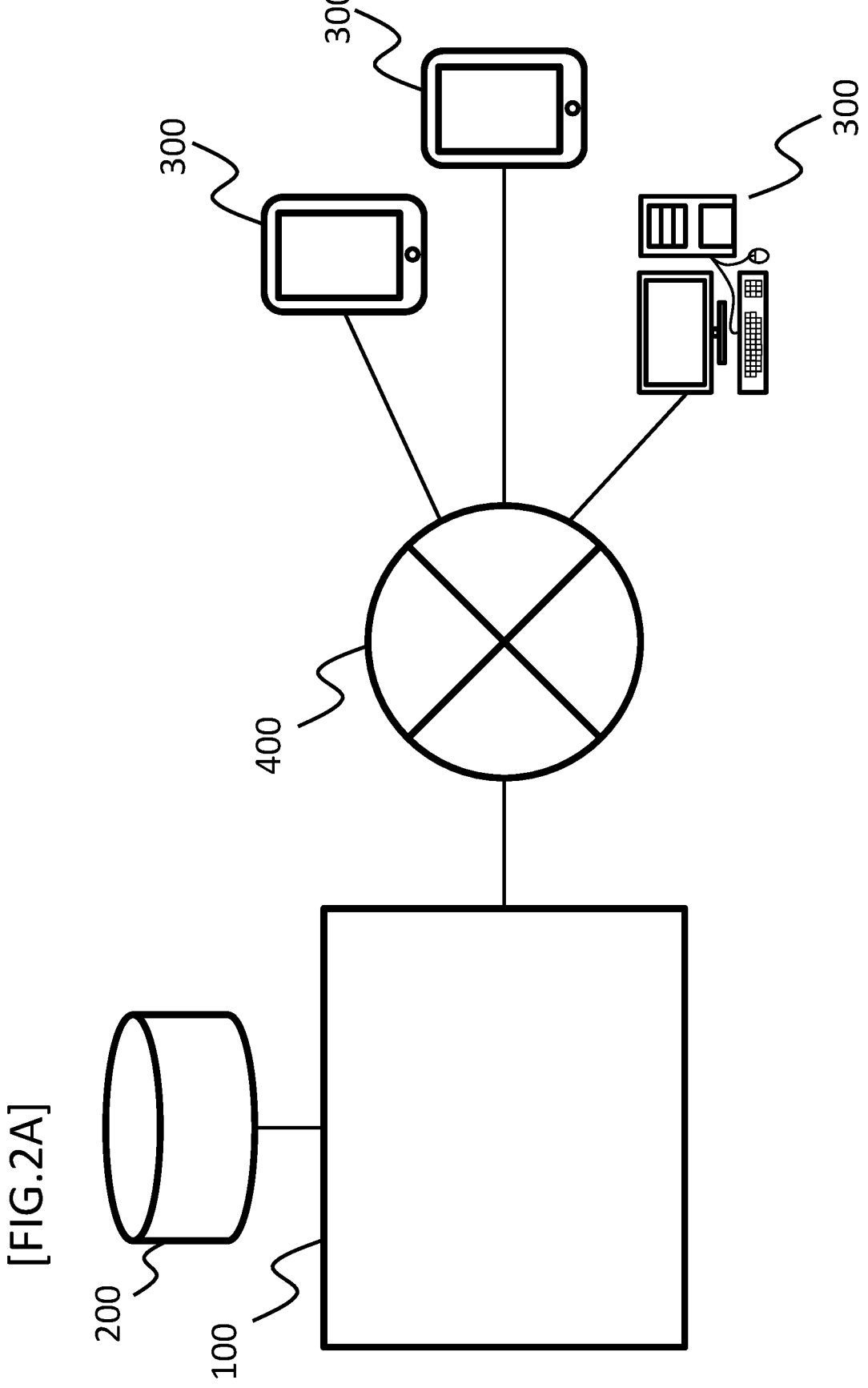

[FIG.2B]
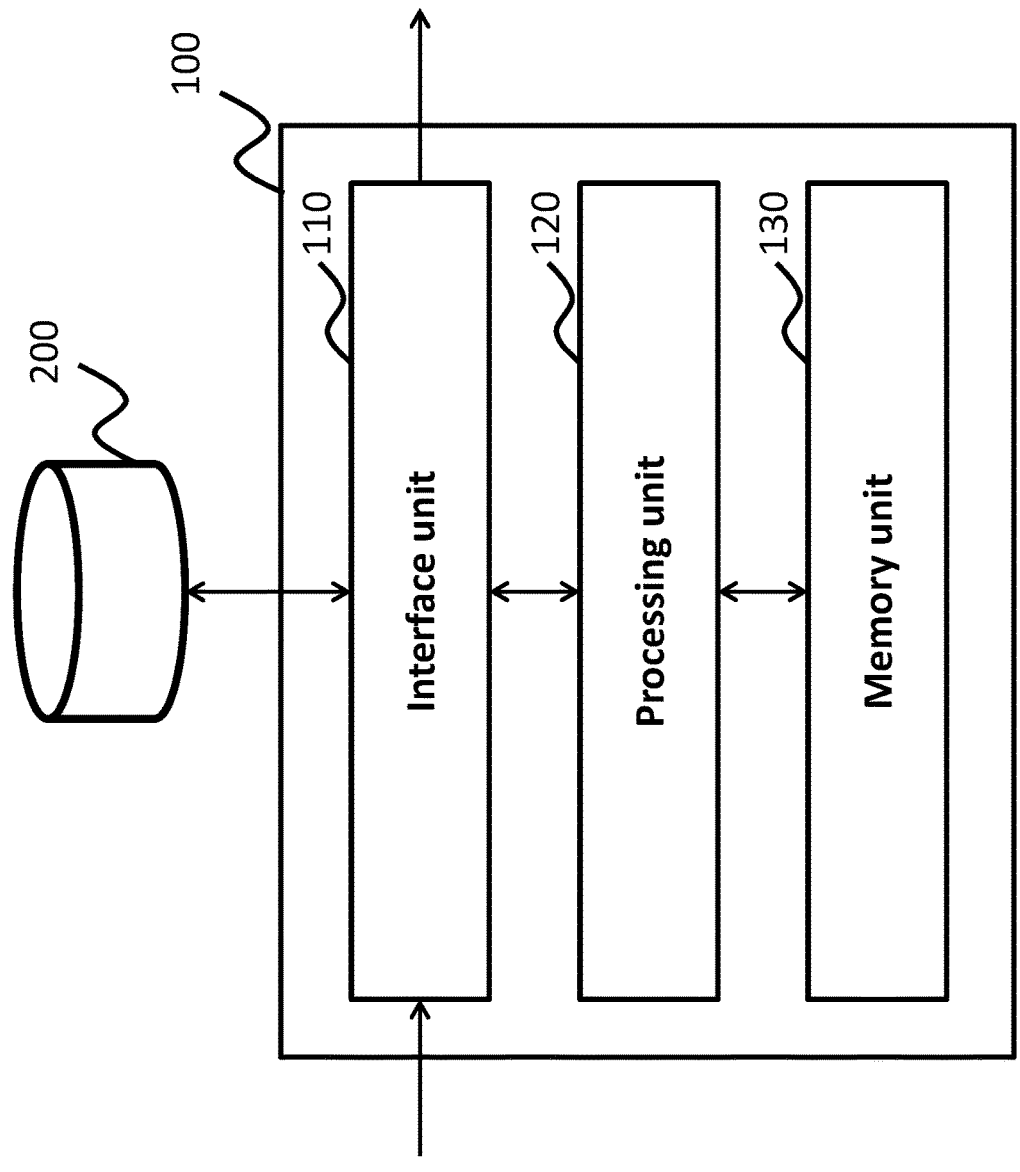

[FIG.2C]
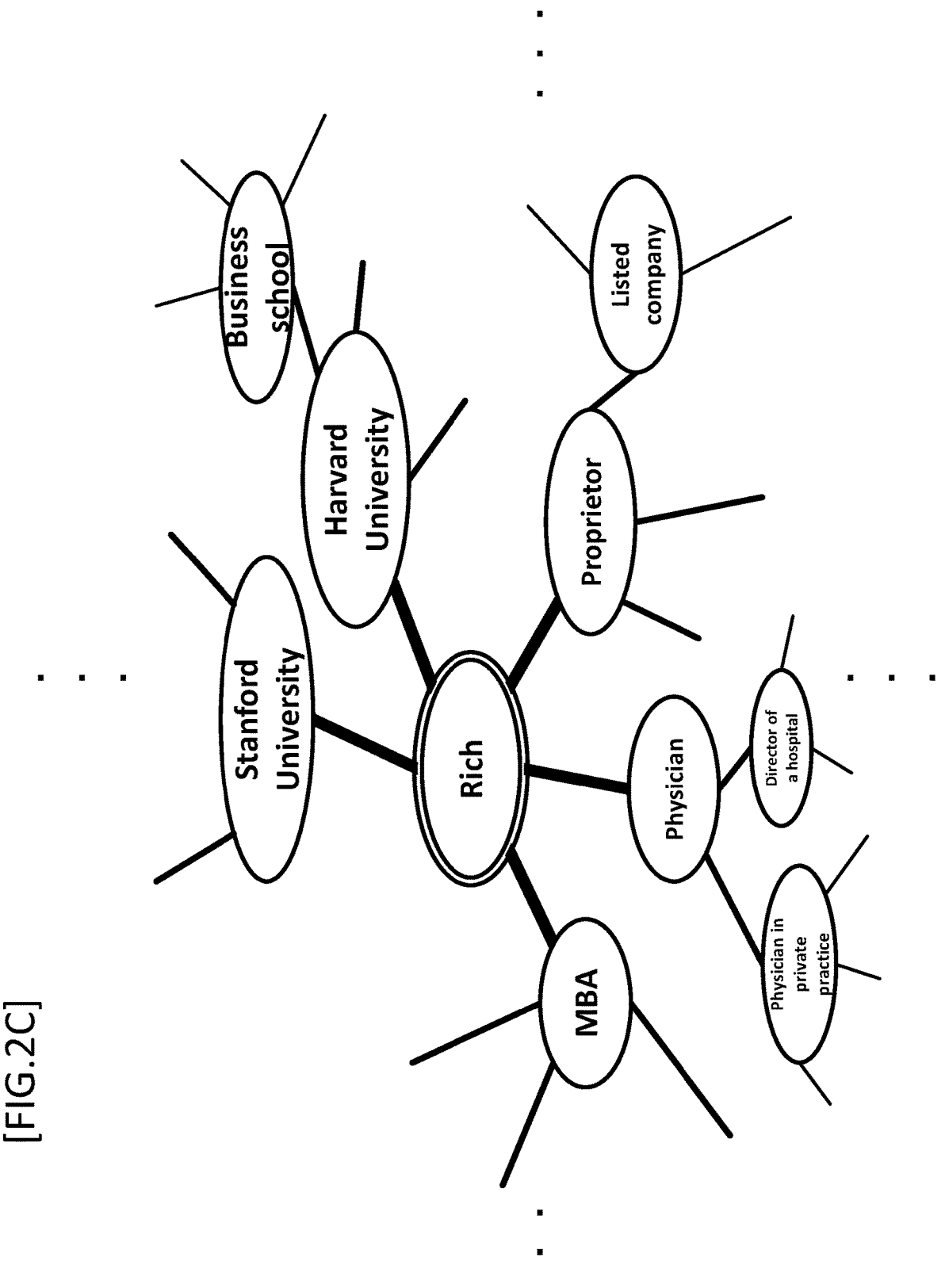

[FIG.3]
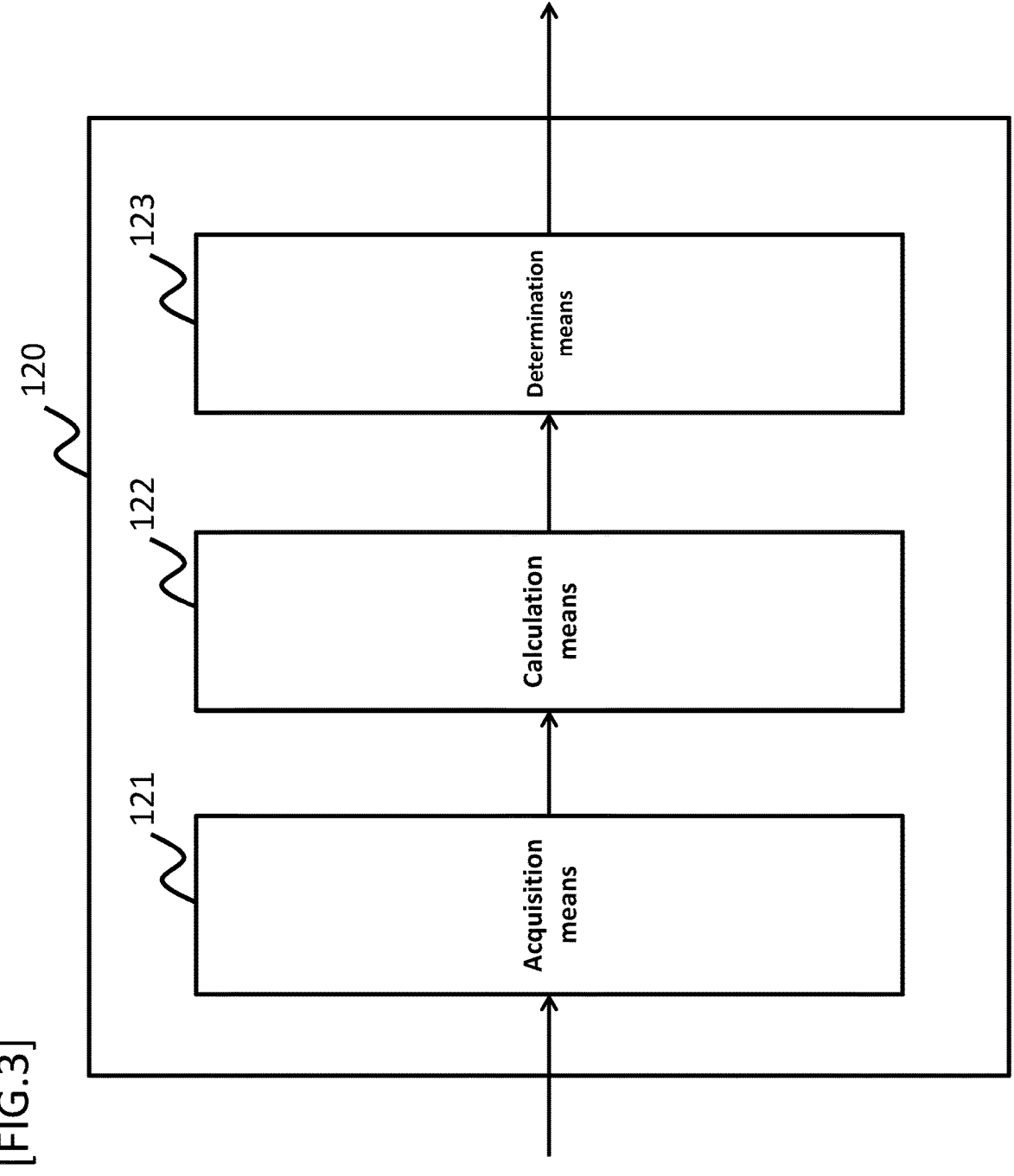

[FIG.4]
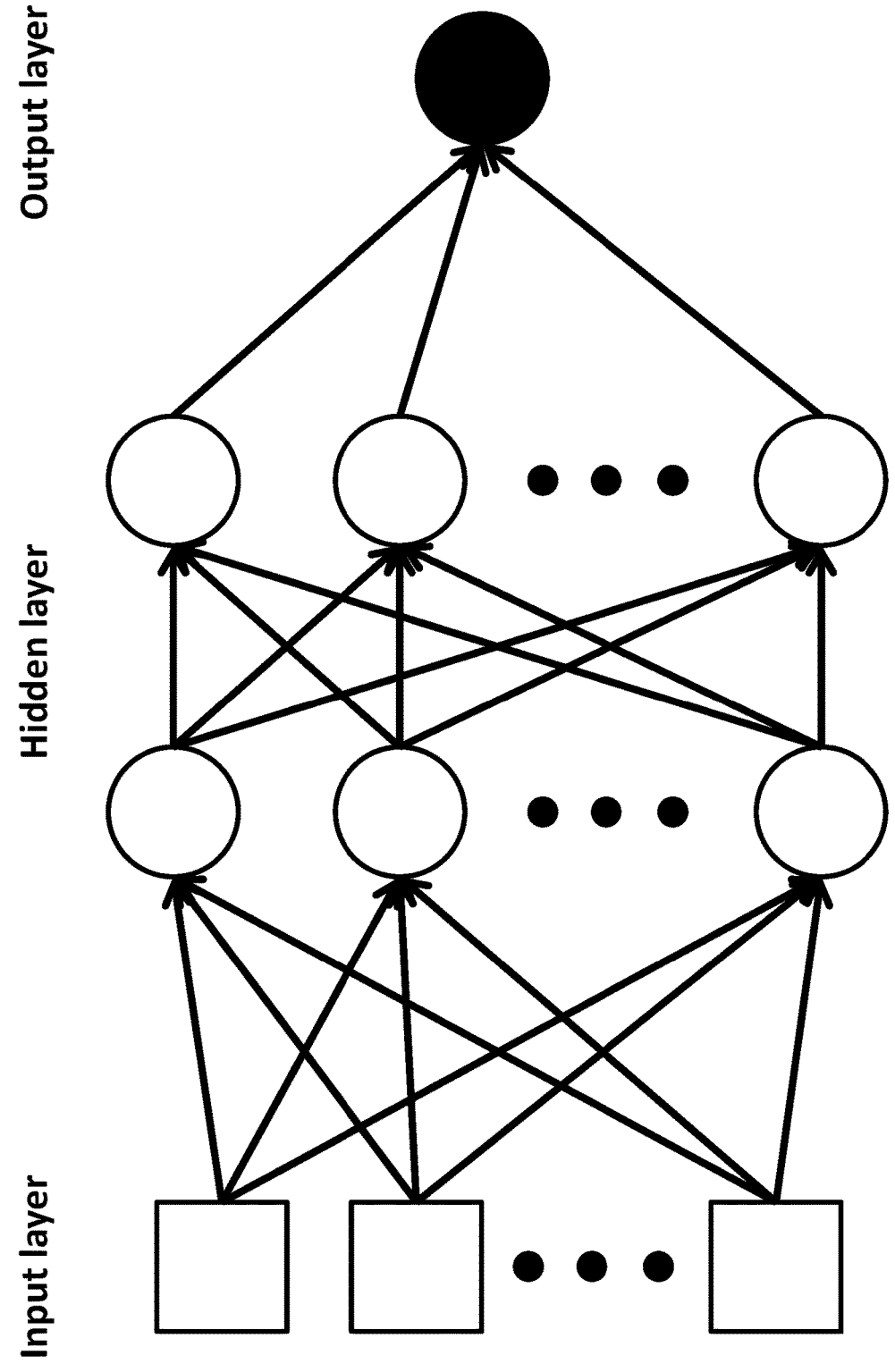
Input layer    Hidden layer    Output layer

[FIG.5]
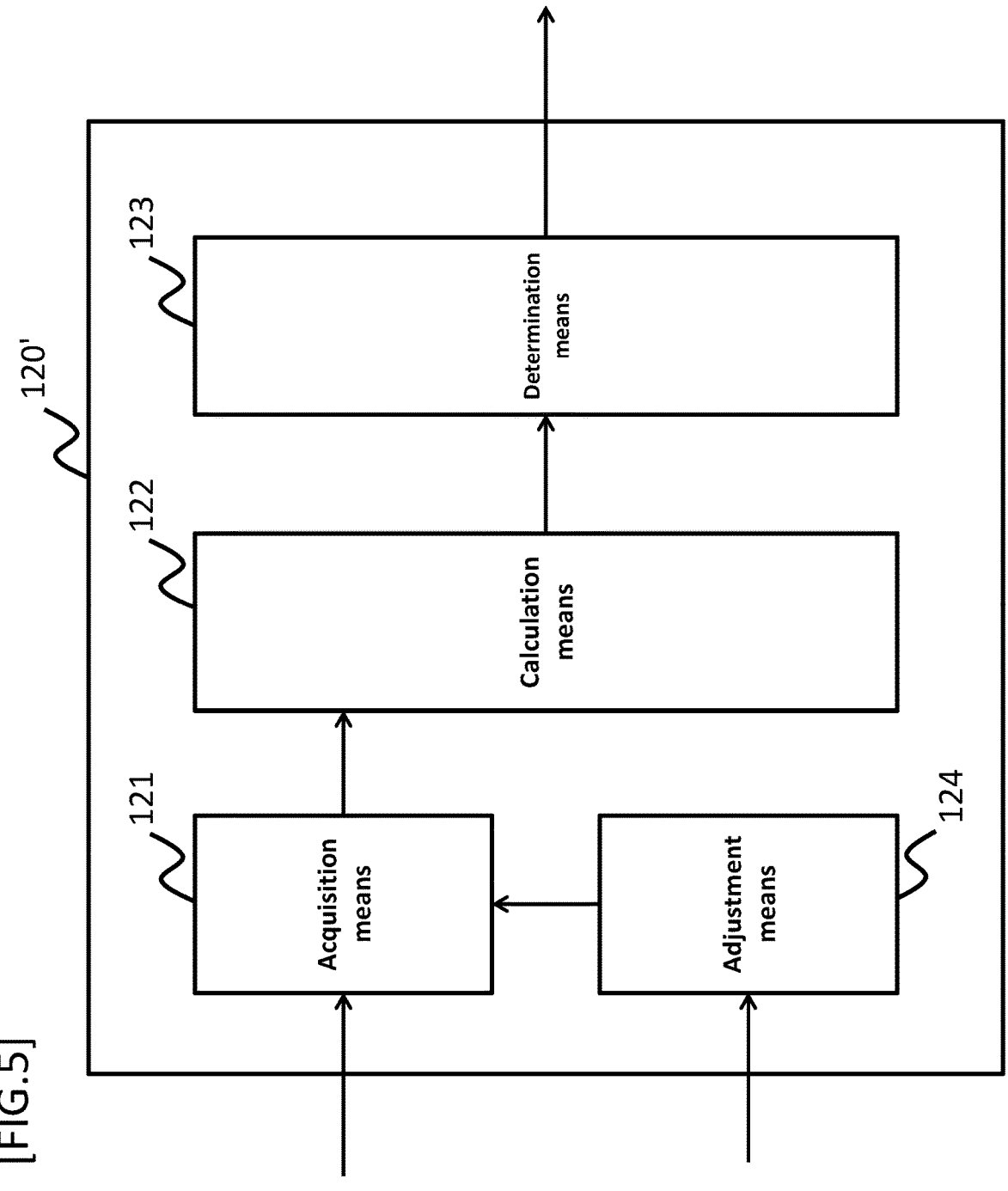

[FIG.6]
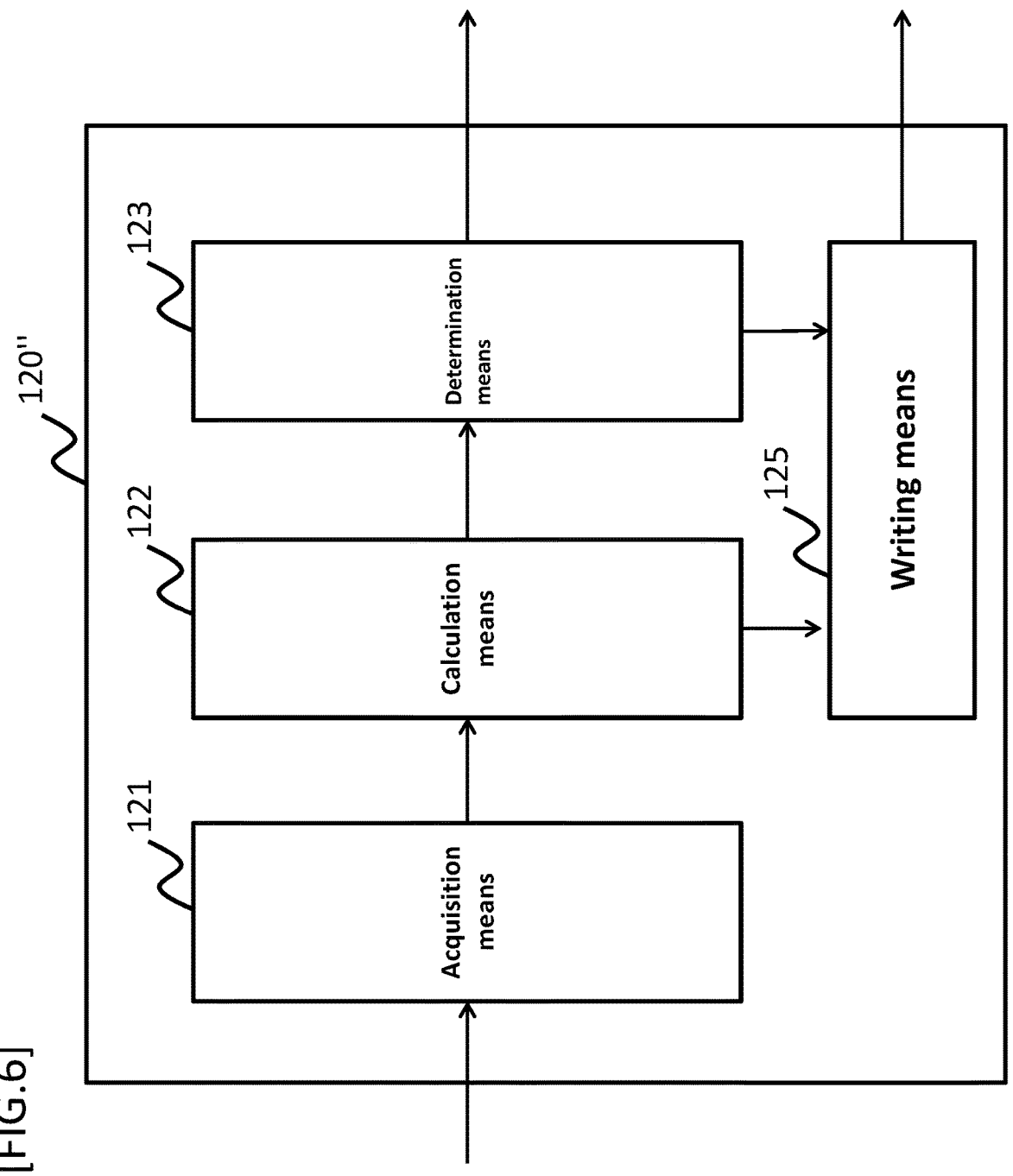

[FIG.7]
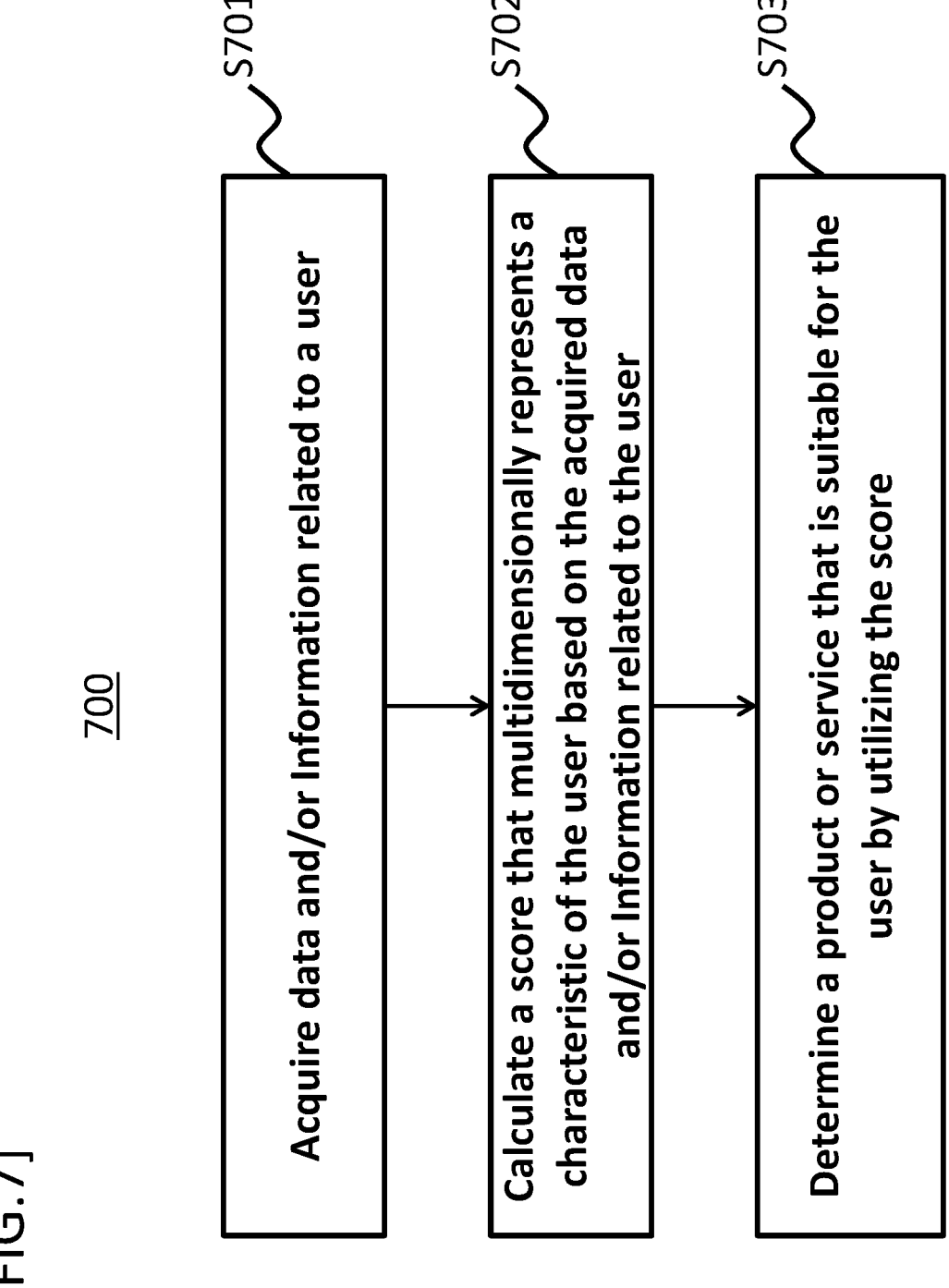
700
S701
Acquire data and/or information related to a user
S702
Calculate a score that multidimensionally represents a characteristic of the user based on the acquired data and/or information related to the user
S703
Determine a product or service that is suitable for the user by utilizing the score

SYSTEM, METHOD, AND PROGRAM FOR DETERMINING COMMODITY OR SERVICE SUITABLE FOR USER

TECHNICAL FIELD

The present invention relates to a system, method, and program for determining a product or service that is suitable for a user.

BACKGROUND ART

A system for recommending a product or service to a user is known (e.g., Patent Literature 1).

CITATION LIST

Patent Literature

[PTL 1] Japanese Laid-Open Publication No. 2008-198163

SUMMARY OF INVENTION

Technical Problem

The objective of the present invention is to provide a system, etc. for determining a product or service that is suitable for a user by a novel approach.

Solution to Problem

The present invention provides, for example, the following items.
(Item 1)
A system for determining a product or service that is suitable for a user, comprising:
  acquisition means for acquiring data and/or Information related to a user;
  calculation means for calculating a score that multidimensionally represents a characteristic of the user based on the acquired data and/or Information related to the user; and
  determination means for determining the product or service that is suitable for the user by utilizing the score.
(Item 2)
The system of item 1, wherein the determination means performs:
  deducing a feature in accordance with a field of the product or the service from the score; and
  determining the product or the service based on the feature.
(Item 3)
The system of item 2, wherein
the system is a system for determining a financial product that is suitable for a user, and
  the feature comprises a feature that can be used to evaluate a risk for the user.
(Item 4)
The system of item 3, wherein
the system is a system for determining an insurance product that is suitable for a user, and
  the feature comprises a feature that can be used to evaluate a health and/or financial risk for the user.

(Item 5)
The system of item 2, wherein
the system is a system for determining a travel plan that is suitable for a user, and
  the feature comprises a feature that can be used to evaluate a behavioral character of the user.
(Item 6)
The system of item 2, wherein
the system is a system for determining a consumable good that is suitable for a user, and
  the feature comprises a feature that can be used to evaluate a preference of the user.
(Item 7)
The system of any one of items 1 to 6, wherein the score comprises a feature that can be used to evaluate whether the user is a person who is trustworthy.
(Item 8)
The system of item 7, wherein the score comprises a feature related to personality, a feature related to money, and a feature related to health.
(Item 9)
The system of any one of items 1 to 8, wherein the calculation means calculates the score in accordance with a degree of correlation of the acquired data and/or Information related to the user with at least one of a concept related to personality, a concept related to money, and a concept related to health.
(Item 10)
The system of any one of items 1 to 8, wherein
the acquisition means further comprises adjustment means for adjusting an acquirable range of the data and/or Information related to the user, and
the calculation means calculates the score in accordance with the acquirable range.
(Item 11)
The system of any one of items 1 to 10, wherein the data and/or Information comprises information stored in a payroll card.
(Item 12)
The system of any one of items 1 to 11, wherein
the system further comprises writing means for writing the score into a token the user owns, and
the determination means is configured to be able to read out the score from the token.
(Item 13)
The system of item 12, wherein the writing means is further configured to write information indicating the determined product or service into the token.
(Item 14)
The system of any one of items 1 to 13, further comprising presentation means for presenting the determined product or service to the user.
(Item 15)
A method for determining a product or service that is suitable for a user, comprising:
  acquiring data and/or Information related to a user;
  calculating a score that multidimensionally represents a characteristic of the user based on the acquired data and/or Information related to the user; and
  determining the product or service that is suitable for the user by utilizing the score.
(Item 15A)
The method of item 15, further comprising a characteristic of any one or more of the preceding items.
(Item 16)
A program for determining a product or service that is suitable for a user, the program being executed in a computer system comprising a processor, the program causing the processor to perform processing comprising:

acquiring data and/or Information related to a user;

calculating a score that multidimensionally represents a characteristic of the user based on the acquired data and/or Information related to the user; and determining the product or service that is suitable for the user by utilizing the score.

(Item 16A)

The program of item 16, further comprising a characteristic of any one or more of the preceding items.

(Item 17)

A system for calculating a score utilized for determining a product or service that is suitable for a user comprising:

acquisition means for acquiring data and/or Information related to a user; and calculation means for calculating a score that multidimensionally represents a characteristic of the user based on the acquired data and/or Information related to the user.

(Item 17A)

The system of item 17, further comprising a characteristic of any one or more of the preceding items.

(Item 18)

A method for calculating a score utilized for determining a product or service that is suitable for a user comprising:

acquiring data and/or Information related to a user; and calculating a score that multidimensionally represents a characteristic of the user based on the acquired data and/or Information related to the user.

(Item 18A)

The method of item 18, further comprising a characteristic of any one or more of the preceding items.

(Item 19)

A program for calculating a score utilized for determining a product or service that is suitable for a user, the program being executed in a computer system comprising a processor, the program causing the processor to perform processing comprising:

acquiring data and/or Information related to a user; and calculating a score that multidimensionally represents a characteristic of the user based on the acquired data and/or Information related to the user.

(Item 19A)

The program of item 19, further comprising a characteristic of any one or more of the preceding items.

Advantageous Effects of Invention

The present invention can determine a product or service that is suitable for a user with high precision by utilizing a score that multidimensionally represents a characteristic of the user, i.e., digital twin of the user.

BRIEF DESCRIPTION OF DRAWINGS

FIG. 1 Diagram showing an example of a flow for determining a product or service that is suitable for a user FIG. 2A Diagram showing an example of a configuration of system 100 for determining a product or service that is suitable for a user FIG. 2B Diagram showing an example of a specific configuration of system 100 for determining a product or service that is suitable for a user FIG. 2C Schematic diagram showing the association of information stored in database unit 200

FIG. 3 Diagram showing an example of a configuration of processing unit 120

FIG. 4 Diagram showing an example of a structure of a neural network model that can be utilized by calculation means 122

FIG. 5 Diagram showing an example of a configuration of processing unit 120', which is an alternative embodiment of processing unit 120.

FIG. 6 Diagram showing an example of a configuration of processing unit 120", which is an alternative embodiment of processing unit 120.

FIG. 7 Diagram showing an example of processing (processing 700) by system 100 for determining a product or service that is suitable for a user.

DESCRIPTION OF EMBODIMENTS

The embodiments of the invention are described hereinafter with reference to the drawings.

1. Service for Determining a Product or Service that is Suitable for a User

The inventor of the invention has developed a new service for determining a product or service that is suitable for a user. The service utilizes a "digital twin" of a user for determining a product or service that is suitable for the user. In this regard, a "digital twin" refers to a subject in real space replicated in a virtual space or digital space. Specifically, a "digital twin" of a user reflects what kind a person the user is, or the nature of the user, in a virtual space or digital space. In this regard, "digital twin" can be expressed as a score that multidimensionally represents a characteristic of the user. In other words, what kind a person the user is, or the nature of the user, can be represented by such a score.

Such a service determines a product or service that is suitable for a digital twin by utilizing the digital twin of a user. Since a generated digital twin reflects the nature of a user, a product or service that is suitable for the digital twin can in turn be deemed as a product or service that is suitable for the user.

FIG. 1 shows an example of a flow for determining a product or service that is suitable for a user.

This example describes that a computer system 100 of a provider providing a service for determining a product or service that is suitable for a user determines a product or service that is suitable for user U.

At step S1, the user U provides data and/or Information related to the user U to the computer system 100.

In this regard, data related to a user refers to objective information related to the user. Data related to a user may be private information known only to the user themselves or public information shared with third parties. Data related to a user can be acquired from, for example, an information terminal apparatus of the user and/or an IoT device that is capable of communicating with an information terminal apparatus of the user. Data related to a user can be acquired from, for example, any place on a network N. For example, data related to a user can be recorded in a token stored at a suitable location on the network N. In this regard, "token" refers to a physical or virtual container that can retain information. It is preferable that information retained in a "token" is retained in the token in a manner that it is difficult to tamper with (e.g., by using a block chain technology), whereby the information retained in the "token" would be valuable. A token can be subjected to distribution, e.g., handled similarly to virtual currency. Examples of data related to a user include, but are not limited to, user's action history (e.g., exercise history, health activity history, purchase history, saving history, dietary history, Web page browsing history, conversation history with an AI speaker, SNS usage history, etc.), health information (e.g., height, weight, blood pressure, heart rate, disease from which the user is suffering, etc.), information related to DNA, insurance coverage information, etc. Data related to a user can include personal information of the user. Examples of personal information include, but are not limited to, at least one of name, address, phone number, email address, age, sex, family structure, occupation, annual income, assets, medical history, etc.

Data related to a user can be acquired from, for example, a payroll card. A payroll card is utilized in a payroll card system. A payroll card system refers to a system that enables payment of wages from an employer to be received electronically (e.g., receive electronic money). A payroll card may be a physical card or a virtual card (e.g., electronic wallet). Payment of wages can be received with a payroll card without involving a bank account. Income information from payment of wages and expenditure information can be recorded onto a payroll card. Furthermore, information related to work-related expenses can also be recorded onto a payroll card. For example, the amount paid as expenses, description thereof, etc. are recorded onto a payroll card. Thus, acquisition of data related to a user from a payroll card enables not only information on private income/expenditure of the user, but also information on work-related income/ expense of the user to be used as data related to the user.

In this regard, Information related to a user refers to subjective information, with the user as the subject. Information related to a user may be private information known only to the user themselves or public information shared with third parties. Information related to a user can be acquired by, for example, direct input into an information terminal apparatus by the user. Information related to a user can be indirectly deduced from the user through, for example, interviews, questions, etc. For example, Information related to a user can be acquired from any place on the network N. For example, Information related to a user can be recorded in a token stored at a suitable location on the network N. Examples of Information related to a user include, but are not limited to, hobbies, preferences, reasons for an action (e.g., reasons for applying for current or past job, reasons for leaving from past job, etc.), etc.

The user U can provide data and/or Information related to the user U to the computer system 100 via, for example, the user's own information terminal apparatus. Alternatively, the user U can provide data and/or Information related to the user U to the computer system 100 via, for example, an IoT device associated with the user U.

In addition to or instead of step S1, the user U transmits an instruction on the network N to provide data and/or Information related to the user U stored on the network N to the computer system 100 at step S2. For example, the user U can transmit an instruction to provide a token stored at a suitable location on the network N to the computer system 100.

At step S3, data and/or Information related to the user U is provided to the computer system 100 from a location on the network N where the data and/or Information related to the user U is stored. For example, a token of the user U is provided to the computer system 100 from a suitable location on a network.

Once the computer system 100 receives data and/or Information related to the user U, the computer system 100 generates a "digital twin" of the user U based on the data and/or Information related to the user U. In this regard, a "digital twin" can be expressed as a score that multidimensionally represents a characteristic of a user. The computer system 100 determines a product or service that is suitable for a "digital twin" of the user U by utilizing the generated "digital twin" of the user U. Since the generated "digital twin" of the user U reflects the nature of the user U, a product or service that is suitable for the digital twin can in turn be deemed as a product or service that is suitable for the user U.

At step S4, the computer system 100 presents the determined product or service that is suitable for the user U, whereby the user U can be aware of a product or service that is suitable for the user.

In this regard, a product or service that is suitable for the user U can be presented to the user U in any manner. In one example, the token provided in step S3 can be provided to the user U or returned to a suitable location on a network after writing a product or service that is suitable for the user U into the token, whereby the token of the user U is updated and enables information on the product or service that is suitable for the user U to be utilized in subsequent processing. In another example, a product or service that is suitable for the user U may be configured to be sold to the user U, whereby the user U can purchase the product or service that is suitable for the user.

The aforementioned computer system 100 can be materialized by a system for determining a product or service that is suitable for a user described below.

2. Configuration of a System for Determining a Product or Service that is Suitable for a User FIG. 2A shows an example of a configuration of the system 100 for determining a product or service that is suitable for a user.

The system 100 is connected to a database unit 200. The system 100 is also connected to at least one user terminal apparatus 300 via a network 400.

FIG. 2A shows three user terminal apparatuses 300, but the number of user terminal apparatuses 300 is not limited thereto. Any number of user terminal apparatuses 300 can be connected to the system 100 via the network 400.

The network 400 can be any type of network. The network 400 may be, for example, the Internet or a LAN. The network 400 may be a wired network or a wireless network.

Examples of the system 100 include, but are not limited to, a computer (e.g., server) installed at a provider providing a service for recommending a product or service. For example, the system may be a computer installed at a provider providing a product or service. Examples of the user terminal apparatus 300 include, but are not limited to, a computer (e.g., terminal apparatus) utilized by a user who is a consumer of a product or service. In this regard, the computer (server or terminal apparatus) can be any type of computer. For example, a terminal apparatus can be any type of terminal apparatus such as a smartphone, tablet, personal computer, smart glass, or smart watch.

The database unit 200 at least stores various pieces of information utilized for calculating a score indicating a characteristic of a user.

FIG. 2B shows an example of a specific configuration of the system 100 for determining a product or service that is suitable for a user.

The system 100 comprises an interface unit 110, a processing unit 120, and a memory unit 130.

The interface unit 110 exchanges information with an element external to the system 100. The processing unit 120 of the system 100 can receive information from an element external to the system 100 and transmit information to an element external to the system 100, via the interface unit 110. The interface unit 110 can exchange information in any form.

The interface unit 110 comprises, for example, an input unit that enables information to be inputted into the system 100. An input unit can enable information to be inputted into the system 100 in any form. If, for example, an input unit is a receiver, information may be inputted by the receiver receiving the information from an element external to the system 100 via a network. Alternatively, if an input unit is a data reading apparatus, information may be inputted by reading out the information from a storage medium connected to the system 100.

The interface unit 110 comprises, for example, an output unit that enables information to be outputted from the system 100. An output unit can enable information to be outputted from the system 100 in any form. If, for example, an output unit is a transmitter, information may be outputted by the transmitter transmitting the information to an element external to the system 100 via a network. Alternatively, if an output unit is a data writing apparatus, information may be outputted by writing the information onto a storage medium connected to the system 100.

The system 100 can, for example, transmit information to the database unit 200 and/or receive information from the database unit 200 via the interface unit 110. The system 100 can, for example, transmit information to the user terminal apparatus 300 and/or receive information from the user terminal apparatus 300 via the interface unit 110.

The system 100 can, for example, receive data and/or Information related to a user via the interface unit 110. As described below, data related to a user is objective information related to the user, and Information related to a user is subjective information, with the user as subject.

The system 100 can receive, for example, a request to determine a suitable product or service via the interface unit 110. A request to determine a suitable product or service may include, for example, a request to purchase some type of a product or service. The system 100 can transmit, for example, information related to the determined product or service via the interface unit 110.

The processing unit 120 executes processing of the system 100 and controls the overall operation of the system 100. The processing unit 120 reads out a program stored in the memory unit 130 and executes the program, whereby the system 100 can function as a system for executing desired steps. The processing unit 120 may be implemented by a single processor or a plurality of processors.

The memory unit 130 stores a program required for the execution of processing of the system 100, data that is required for the execution of the program, etc. The memory unit 130 may store a program for causing the processing unit 120 to perform processing for determining a product or service that is suitable for a user (e.g., program for materializing the processing described below in FIG. 7). In this regard, a program can be stored in the memory unit 130 in any manner. For example, a program may be pre-installed in the memory unit 130. Alternatively, a program may be configured to be installed into the memory unit 130 by download through a network. In such a case, the network can be of any type. The memory unit 130 can be implemented by any storage means.

For example, data and/or Information related to a user can be stored in the database unit 200.

Data related to a user is objective information related to the user. Data related to a user may be private information known only to the user themselves or public information shared with third parties. Data related to a user can be acquired from, for example, an information terminal apparatus of the user and/or an IoT device that is capable of communicating with an information terminal apparatus of the user. Data related to a user can be acquired from, for example, any place of the network N. For example, data related to a user can be recorded in a token stored at a suitable location on the network N. Examples of data related to a user include, but are not limited to, user's action history (e.g., exercise history, health activity history, purchase history, saving history, dietary history, Web page browsing history, conversation history with an AI speaker, SNS usage history, etc.), health information (e.g., height, weight, blood pressure, heart rate, disease from which the user is suffering, etc.), information related to DNA, insurance coverage information, etc. Data related to a user can include personal information of the user. Examples of personal information include, but are not limited to, at least one of name, address, phone number, email address, age, sex, family structure, occupation, annual income, assets, medical history, etc.

Data related to a user can be acquired from, for example, a payroll card. A payroll card system refers to a system that enables payment of wages from an employer to be received electronically. Payment of wages can be received with a payroll card without involving a bank account. Income information from payment of wages and expenditure information can be recorded onto a payroll card. Furthermore, information related to work-related expenses can also be recorded onto a payroll card. For example, the amount paid as expenses, description thereof, etc. are recorded onto a payroll card. Thus, acquisition of data related to a user from a payroll card enables not only information on private income/expenditure of the user, but also information on work-related income/expense of the user to be used as data related to the user.

Information related to a user is subjective information, with the user as the subject. Information related to a user may be private information known only to the user themselves or public information shared with third parties. Information related to a user can be acquired by, for example, direct input into information terminal an apparatus by the user. Information related to a user can be indirectly deduced from the user through, for example, interviews, questions, etc. For example, Information related to a user can be acquired from any place on the network N. For example, Information related to a user can be recorded in a token stored at a suitable location on the network N. Examples of Information related to a user include, but are not limited to, hobbies, preferences, reasons for an action (e.g., reasons for applying for current or past job, reasons for leaving from past job, etc.), etc.

The database unit 200 stores various pieces of information utilized for calculating a score that represents a characteristic of a user.

In this regard, the characteristic of the user can be a concept representing what kind of person the user is, i.e., the nature of the user. A characteristic of a user can also represent the nature of the user from a viewpoint of whether the user is a trustworthy person. For example, a characteristic of a user can represent the nature of the user from the viewpoint related to "personality" and/or the viewpoint related to "money" and/or the viewpoint related to "health". Thus, a score that multidimensionally represents a characteristic of a user can comprise a feature related to "personality" and/or a feature related to "money" and/or a feature related to "health". Multidimensional axes of a score can comprise, for example, an axis from the viewpoint related to "personality", and axis from the viewpoint related to "money", and/or an axis from the viewpoint related to "health". In this regard, "personality" is information representing whether the character and/or make-up of the person is trustworthy. Personality includes, for example, evaluation from others. "Money" is information related to money of the person. Examples thereof include information such as annual income, assets, and whether the person is frugal. "Health" is information related to the health of the person. Examples thereof include information such as diseases, dietary habit, and activity for health.

If a score that represents a characteristic of a user has an axis from the viewpoint related to "personality" in one example, points are given for a plurality of items related to "personality", and the nature of the person related to "personality" would be represented based on the points for each of the plurality of items. For example, among items related to "personality", a person who is hot-tempered but has an honest character has many points for the item related to "honest person" or few points for the item related to "liar" and many points for the item related to "short-tempered" or few points for the item related to "patient".

If a score that represents a characteristic of a user has an axis from the viewpoint related to "money" in another example, points are given for a plurality of items related to "money", and the nature of the person related to "money" would be represented based on the points for each of the plurality of items. For example, among items related to "money", a person who often squanders money has many points for the item related to "frugal spender" or few points for the item related to "big spender".

If a score that represents a characteristic of a user has an axis from the viewpoint related to "health" in another example, points are given for a plurality of items related to "health", and the nature of the person related to "health" would be represented based on the points for each of the plurality of items. For example, among items related to "health", a person with an obese physique has many points for the item related to "degree of obesity" or "BMI".

These items are just examples. Each of the multidimensional axes can have any item. With a higher number of items each axis has, the nature of a user can be represented more precisely for the viewpoint of the axis, but the amount of data would be greater accordingly. With fewer items each axis has, the amount of data for a score that represents a characteristic of a user would be less and easier to handle, but the nature of the user would be more roughly represented. For example, a score that represents a characteristic of a user may be a score deduced by extracting a specific item for at least two of the plurality of axes (score that roughly represents the nature of a user) from a score represented for a plurality of axes having a large number of items (score that represents the nature of a user in detail).

For example, a concept related to a parameter used for the calculation of a score can be stored while being associated with various pieces of information in the database unit 200. A parameter used in the calculation of a score can comprise, for example, "personality", "money", or "health".

For example, for the parameter of "personality", a concept related to personality can be stored while being associated with various pieces of information in the database unit 200. For example, the concept of "altruistic" (or "transpersonal") related to "personality" can be stored while being associated with a keyword such as "volunteer", "donation", "consideration", or "consultation", status such as "frequently participates in volunteer events", "frequently consulted", or "have experience with donating", etc. For example, the concept of "SDGs" (Sustainable Development Goals) related to "personality" can be stored while being associated with a keyword associated with 17 goals and/or 169 targets (e.g., "equality", "environmental conservation", etc.), status such as "taking action associated with 17 goals and/or 169 targets" or "have ideology associated with 17 goals and/or 169 targets", etc.

For example, for the parameter of "money", a concept related to money can be stored while being associated with various pieces of information in the database unit 200. For example, the concept of "rich" (or "cash flow rich") related to "money" can be stored while being associated with a keyword such as "Harvard University" or "MBA", status such as "annual income of 20 million yen or more", etc. For example, the concept of "rich" (or "rich from related to "money" can be stored while being stocks") associated with a keyword such as "landlord" or "stockholder", status such as "asset of one hundred million yen or more", etc.

For example, for the parameter of "health", a concept related to health can be stored while being associated with various pieces of information in the database unit 200. For example, the concept of "excellent body" (or "physical health") related to "health" can be stored while being associated with a keyword such as "non-smoking" or "normal blood pressure", status such as "BMI 18 to 27", etc. For example, the concept of "mindfulness" (or "mental health") related to "health" can be stored while being associated with a keyword such as "sense of reward" or "stress-free", status such as "result of stress check is less than a predetermined value" or "high sense of coherence (SOC)", etc.

FIG. 2C is a schematic diagram showing the association of information stored in database unit 200.

In the example shown in FIG. 2C, the concept of "rich" related to money is associated with a keyword such as "Harvard University", "Stanford University", "MBA", "physician", or "proprietor". Another keyword (e.g., "business school", "physician in private practice", "listed company", etc.) is further associated with these keywords. Yet, another keyword can be further associated with these keywords.

Such association can be performed by using, for example, artificial intelligence (AI) that is capable of semantic search, i.e., artificial intelligence that has learned the correlation between keywords.

Such artificial intelligence has learned the correlation between keywords from a large amount of text. For example, such artificial intelligence extracts a plurality of keywords in texts by syntactic analysis of the texts and identifies the relationship between the plurality of keywords in the texts. If, for example, a certain keyword is used concurrently with another keyword in many texts, such artificial intelligence learns such keywords as keywords with strong correlation. Artificial intelligence that has learned the correlation between keywords in this manner can output a keyword correlated with an inputted keyword based on the learned correlation.

If, for example, the keyword of "rich" is inputted into artificial intelligence that has learned the correlation between "Harvard keywords, University", "Stanford University", "MBA", "physician", "proprietor", etc. can be outputted as a keyword correlated with "rich". If, for example, the keywords "rich" and "physician" are inputted into artificial that intelligence has learned the correlation between keywords, "physician in private practice", "director of a hospital", etc. can be outputted as a keyword correlated with "rich" and "physician".

In this manner, a keyword inputted into artificial intelligence that has learned the correlation between keywords can be stored while being associated with an outputted keyword in the database unit 200.

In the examples shown in FIG. 2A and FIG. 2B, the database unit 200 is provided external to the system 100, but the present invention is not limited thereto. At least a portion of the database unit 200 can also be provided inside the system 100. At this time, at least a part of the database unit 200 may be implemented by the same storage means as, or different storage means from, storage means implementing the memory unit 130. In either case, at least a portion of the database unit 200 is configured as a storage section for the system 100. The configuration of the database unit 200 is not limited to a specific hardware configuration. For example, the database unit 200 may be comprised of a single hardware part or a plurality of hardware parts. For example, the database unit 200 may be configured as an external hard disk apparatus of the system 100, storage on the cloud connected via a network, or a dispersed network utilizing a block chain technology, etc.

For example, data and/or Information related to a user is stored in the database unit 200 configured as a decentralized network utilizing a block chain technology, etc. At this time, the data and/or Information related to the user is substantially impossible to tamper with, whereby reliability of the data and/or Information related to the user is ensured.

FIG. 3 shows an example of a configuration of the processing unit 120.

The processing unit 120 comprises acquisition means 121, calculation means 122, and determination means 123.

The acquisition means 121 is configured to acquire data and/or Information related to a user.

The acquisition means 121 may be configured to, for example, acquire data and/or Information related to a user stored in the database unit 200 via the interface unit 110. Alternatively, the acquisition means 121 may be configured to, for example, acquire data and/or Information related to a user received from the user terminal apparatus 300 via the interface unit 110. Alternatively, the acquisition means 121 may be configured to, for example, acquire data and/or Information related to a user from a given location on a network. For example, the acquisition means 121 can acquire data related to a user from a payroll card of the user (or a server managing a payroll card). Acquired data and/or Information related to a user is passed onto the calculation means 122.

The calculation means 122 is configured to calculate a score that multidimensionally represents a characteristic of a user based on data and/or Information related to the user. A characteristic of a user can be a concept representing what kind a person the user is, or the nature of the user. A characteristic of a user can also represent the nature of the user from the viewpoint of whether the user is a trustworthy person. For example, a characteristic of a user can represent the nature of the user from the viewpoint related to "personality" and/or viewpoint related to "money" and/or viewpoint related to "health". Thus, a score that multidimensionally represents a characteristic of a user can comprise a feature related to "personality" and/or a feature related to "money" and/or a feature related to "health". While the term "digital twin" is known, a score that multidimensionally represents a characteristic of a user can be deemed as a score that represents a digital twin of the user.

Multidimensional axes of a score can comprise, for example, an axis from the viewpoint related to "personality", an axis from the viewpoint related to "money", and/or an axis from the viewpoint related to "health".

A score that multidimensionally represents a characteristic of a user can comprise, for example, a feature that can be used to evaluate whether the user is a trustworthy person. For example, with more trustworthy character and/or make-up of a user, more features related to "personality" indicating that the user is a trustworthy person would be included in a score that multidimensionally represents a characteristic of the user. For example, with a more trustworthy point of view, behavior, and/or state related to money of a user, more features related to "money" indicating that the user is a trustworthy person would be included in a score that multidimensionally represents a characteristic of the user. For example, with a more trustworthy point of view, behavior, and/or state related to health of a user, more features related to "health" indicating that the user is a trustworthy person would be included in a score that multidimensionally represents a characteristic of the user.

In one embodiment, the calculation means 122 can, for example, calculate a score in accordance with the degree of correlation of data and/or Information related to a user with a parameter used in the calculation of the score. For example, the calculation means 122 determines the degree of correlation of data and/or Information related to a user with a concept related to a parameter used in a calculation of a score by referring to the database unit 200 storing various pieces of information correlated with the concept related to the parameter used in the calculation of the score. Data and/or Information related to a user can comprise, for example, information related to "personality", "money", or "health".

The calculation means 122 can, for example, determine the degree of correlation of data and/or Information related to a user with a concept related to "personality" and calculate a score in accordance with the determined degree of correlation. If, for example, data and/or Information related to a user is significantly correlated with a specific concept concepts related to among "personality", the calculation means 122 can include a feature corresponding to the concept in a score, or increase the points for the item corresponding to the concept. For example, with stronger correlation of data and/or Information related to a user with "altruistic" (or "transpersonal"), a feature corresponding to "altruistic" can be included more or more strongly in a score, or the points for the item corresponding to "altruistic" can be increased. For example, with a stronger correlation of data and/or Information related to a user with "SDGs" (or "Sustainable Development Goals"), a feature corresponding to "SDGs" can be included more or more strongly in a score, or the points for the item corresponding to "SDGs" can be increased.

The calculation means 122 can, for example, determine the degree of correlation of data and/or Information related to a user with a concept related to "money" and calculate a score in accordance with the determined degree of correlation. If, for example, data and/or Information related to a user is significantly correlated with a specific concept among concepts related to "money", the calculation means 122 can include a feature corresponding to the concept in a score, or increase the points for the item corresponding to the concept. For example, with stronger correlation of data and/or Information related to a user with "cash flow rich", a feature corresponding to "cash flow rich" can be included more or more strongly in a score, or the points for the item corresponding to "cash flow rich" can be increased. For example, with a stronger correlation of data and/or Information related to a user with "rich from stocks", a feature corresponding to "rich from stocks" can be included more or more strongly in a score, or the points for the item corresponding to the concept of "rich from stocks" can be increased.

The calculation means 122 can, for example, determine the degree of correlation of data and/or Information related to a user with a concept related to "health" and calculate a score in accordance with the determined degree of correlation. If, for example, data and/or Information related to a user is significantly correlated with a specific concept among concepts related to "health", the calculation means 122 can include a feature corresponding to the concept in a score, or increase the points for the item corresponding to the concept. For example, with stronger correlation of data and/or Information related to a user with "excellent body" (or "physical health"), a feature corresponding to "excellent body" can be included more or more strongly in a score, or the points for the item corresponding to the concept of "excellent body" can be increased. For example, with a stronger correlation of data and/or Information related to a user with "mindfulness" (or "mental health"), a feature corresponding to "mindfulness" (or "mental health") can be included more or more strongly in a score, or the points for the item corresponding to the concept of "mindfulness" can increased.

In one embodiment, the calculation means 122 can, for example, calculate a score that multidimensionally represents a characteristic of a user by utilizing a machine learning model, which has learned the relationship between data and/or Information related to a plurality of users with a score. Data and/or Information related to a user can comprise, for example, information related to "personality", "money", or "health".

A machine learning model can be constructed by using any machine learning model. A machine learning model can be, for example, a neural network model.

FIG. 4 shows an example of a structure of a neural network model that can be utilized by the calculation means 122.

A neural network model has an input layer, at least one hidden layer, and an output layer. The number of nodes of an input layer of a neural network model corresponds to the number of dimensions of inputted data and/or Information related to a user. A hidden layer of a neural network model can comprise any number of nodes. The number of nodes of an output layer of a neural network model corresponds to the number of dimensions of outputted data. If, for example, a score that multidimensionally represents a characteristic of a user is outputted, the number of nodes of an output layer can be 1.

A neural network model can learn in advance by using data and/or Information related to a user acquired by the acquisition means 121. Learning processing is processing for calculating a weighting coefficient of each node of a hidden layer of a neutral network model by using data and/or Information related to a user acquired in advance by the acquisition means 121.

Learning processing is, for example, supervised learning. In supervised learning, a machine learning model capable of correlating data and/or Information related to a user with a score can be constructed by, for example, using the data and/or Information related to the user as input supervisor data, using a score that multidimensionally represents a characteristic of the user as output supervisor data, and calculating a weighting coefficient of each node of a hidden layer of a neutral network model through use of information on a plurality of users.

For example, a set of (input supervisor data, output supervisor data) for supervised learning can be (data and/or Information related to the first user, first user score), (data and/or Information related to the second user, second user score) . . . (data and/or Information related to the ith user, ith user score) . . . , etc. If data and/or Information related to a user that is newly acquired from the user is inputted into an input layer of such a learned neural network model, a score for the user is outputted to an output layer.

Supervised learning can use, for example, the degree of correlation of data and/or Information related to a user with a parameter used in the calculation of a score as input supervisor data.

The calculated score is passed onto the determination means 123.

Referring back to FIG. 3, the determination means 123 is configured to determine a product or service that is suitable for a user by utilizing a score calculated by the calculation means 122. In one example, a specific product or service is associated with each of a plurality of features that can be contained in a score, and the determination means 123 can determine a product or service corresponding to a feature contained in a score as a product or service that is suitable for a user.

In another example, the determination means 123 can deduce a specific feature from a score and determine a product or service based on the deduced feature. For example, a specific product or service is associated with each of a plurality of features that can be deduced from a score, and the determination means 123 can determine a product or service corresponding to the feature deduced from the score as a product or service that is suitable for a user. For example, a specific product or service is associated with each combination of several of a plurality of features that can be deduced from a score, and the determination means 123 can determine a product or service corresponding to the combination of features deduced from the score as a product or service that is suitable for a user.

The determination means 123 can deduce a specific feature from a score by any approach. In one example, the determination means 123 can extract a specific feature from features contained in a score. In this regard, extraction of a feature means drawing out a feature in the same state without changing the value of the feature. In another example, the determination means 123 can deduce a specific feature by applying a specific function to a score or a feature contained in a score. In this regard, the specific function can be any function. For example, a specific function can be a hash function.

A feature extracted from a score can be changed in accordance with the field of the determined product or service. For example, the determination means 123 can extract a specific feature in accordance with the field of the determined product or service from features contained in a score. For example, the determination means 123 can deduce a specific feature by applying a specific function in accordance with the field of the determined product or service to a score or a feature contained in a score. The system 100 would be able to determine a product or service that is suitable for a user for the specific product or service by tuning a feature deduced from a score for the field of the specific product or service.

A system for determining a product or service that is suitable for a user can be tuned to determine, for example, product that is suitable for a user, an a financial insurance product that is suitable for a user, a travel plan that is suitable for a user, or a consumer good that is suitable for a user. The system of the invention is not limited to determining such products or services, but can be utilized for determining any other product or service.

(System for Determining a Financial Product that is Suitable for a User)

In one example, the system 100 can be configured as a system for determining a financial product that is suitable for a user. In this regard, the financial product refers to a product or a group of products that is used in a financial transaction. Examples of the financial product include products available from a bank, insurance company, stock brokerage firm, etc. such as bank deposits, mutual funds, insurance products, stocks, bonds, foreign exchange, loans, virtual currencies, commodities, and combinations thereof.

In such a system, the determination means 123 can determine a financial product that is suitable for a user by utilizing a score. The determination means 123 can deduce a feature which is useful for determining a financial product that is suitable for a user from a score. For example, the determination means 123 can extract a feature which is useful for determining a financial product that is suitable for a user from a feature contained in a score. For example, the determination means 123 can deduce a feature which is useful for determining a financial product that is suitable for a user by applying a function, which is unique to the field of financial products, to a score or a feature contained in a score.

A feature which is useful for determining a financial product that is suitable for a user preferably comprises a feature which can be used to evaluate the risk for a user. This is because, since risk evaluation for a purchaser has a significant impact on the determination of a financial product, a determined financial product can be more suitable for the user by considering the risk for the user. A feature which can be used to evaluate a risk for a user may be, for example, a feature that is empirically used in the financial industry or a feature that is deduced from machine learning (e.g., cluster analysis, etc.).

If, for example, a feature which is useful for determining a financial product that is suitable for a user indicates that the user has a character of being willing to take risks, a financial product with a high risk-high return profile can be determined as a suitable financial product for the user.

(System for Determining an Insurance Product that is Suitable for a User)

In one example, the system 100 can be configured as a system for determining an insurance product that is suitable for a user. An insurance product has various conditions such as coverage, insurance premium, and optional policy. Determination of an insurance product that is suitable for a user also comprises determining various conditions such as coverage, insurance premium, and optional policy.

In such a system, the determination means 123 can determine an insurance product that is suitable for a user a score. The determination means 123 can by utilizing deduce a feature which is useful for determining an insurance product that is suitable for a user from a score. For example, the determination means 123 can extract a feature which is useful for determining an insurance product that is suitable for a user from a feature contained in a score. For example, the determination means 123 can deduce a feature which is useful for determining an insurance product that is suitable for a user by applying a function, which is unique to the field of insurance products, to a score or a feature contained in a score.

A feature which is useful for determining an insurance product that is suitable for a user preferably comprises a feature which can be used to evaluate the health and/or financial risk for a user. This is because, since a health and/or financial risk for a subscriber has a significant impact on the determination of an insurance product, a determined insurance product can be more suitable for a user by considering the health and/or financial risk for the user. A feature which can be used to evaluate a risk for a user may be, for example, a feature that is empirically used in the insurance industry or a feature that is deduced from machine learning (e.g., cluster analysis, etc.).

If, for example, a feature which is useful for determining an insurance product that is suitable for a user indicates that the user does not exercise sufficiently, an insurance product including health insurance with an optional policy for cancer insurance can be determined as a suitable insurance product for the user.

(System for Determining a Travel Plan that is Suitable for a User)

In one example, the system 100 can be configured as a system for determining a travel plan that is suitable for a user. A travel plan has various conditions such as destination, transportation means, activity, and schedule. Determination of a travel plan that is suitable for a user also comprises determining various conditions such as destination, transportation means, activity, and schedule.

In such a system, the determination means 123 can determine a travel plan that is suitable for a user by utilizing a score. The determination means 123 can deduce a feature which is useful for determining a travel plan that is suitable for a user from a score. For example, the determination means 123 can extract a feature which is useful for determining a travel plan that is suitable for a user from a feature contained in a score. For example, the determination means 123 can deduce a feature which is useful for determining a travel plan that is suitable for a user by applying a function, which is unique to the field of travel plan, to a score or a feature contained in a score.

A feature which is useful for determining a travel plan that is suitable for a user preferably comprises a feature which can be used to evaluate the behavioral character of the user. This is because, since a behavioral character of a traveler has a significant impact on the determination of a travel plan, a determined travel plan can be more suitable for a user by considering the behavioral character of the user. A feature which can be used to evaluate a behavioral character of a user may be, for example, a feature that is empirically used in the tourism industry or a feature that is deduced from machine learning (e.g., cluster analysis, etc.).

If, for example, a feature which can be used to evaluate the behavioral character of a user indicates that the user has a character of being adventurous, a travel plan including activities for exploring nature can be determined as a suitable travel plan for the user.

(System for Determining a Consumer Good that is Suitable for a User)

In one example, the system 100 can be configured as a system for determining a consumer good that is suitable for a user. A consumer good refers to a product that is purchased by a consumer for the purpose of consumption within the household budget. Consumer goods include durable consumer goods which are used over a long period of time and non-durable consumer goods which are consumed in single use.

In such a system, the determination means 123 can determine a consumer good that is suitable for a user by utilizing a score. The determination means 123 can deduce a feature which is useful for determining a consumer good that is suitable for a user from a score. For example, the determination means 123 can extract a feature which is useful for determining a consumer good that is suitable for a user from a feature contained in a score. For example, the determination means 123 can deduce a feature which is useful for determining a consumer good that is suitable for a user by applying a function, which is unique to the field of consumer goods, to a score or a feature contained in a score.

A feature which is useful for determining a consumer good that is suitable for a user preferably comprises a feature which can be used to evaluate the preference of the user. This is because, since the preference of a consumer has a significant impact on the determination of a consumer good, a determined consumer good can be more suitable for a user by considering the preference of the user. A feature which can be used to evaluate the risk for a user may be, for example, a feature that is empirically used in the industry of manufacture and sale of consumer goods or a feature that is deduced f from machine learning (e.g., cluster analysis, etc.).

If, for example, a feature which can be used to evaluate the preference of a user indicates that the user prefers classic styles, a consumer good with a design that was popular in the past can be determined as a suitable consumer good for the user.

For example, a product or service that is suitable for a user, which has been determined by the determination means 123, is outputted from the processing unit 120 to an element external to the system 100 via the interface unit 110. Such an output can be utilized in any application. For example, the determined product or service that is suitable for a user can be presented to the user. Alternatively, only information indicating the determined product or service that is suitable for a user, etc. can be presented to the user. Alternatively, a recommendation for a product or service based on the determined product or service that is suitable for a user, etc. can be presented to the user.

FIG. 5 shows an example of a configuration of a processing unit 120', which is an alternative embodiment of the processing unit 120.

The processing unit 120' has the same configuration as the processing unit 120, except in terms of comprising adjustment means 124. In FIG. 5, a constituent element that is identical to the configuration described above in reference to FIG. 3 is assigned with the same reference number, and descriptions thereof are omitted in this section.

The processing unit 120' comprises acquisition means 121, calculation means 122, determination means 123, and adjustment means 124.

The adjustment means 124 is configured to adjust the range of data and/or Information related to a user which can be acquired by the acquisition means 121. The adjustment means 124 can adjust the acquirable range of data and/or Information related to a user in any manner. For example, the adjustment means 124 can adjust the acquirable range of data and/or Information related to a user by designating data and/or Information related to a user, which is prohibited from being acquired by the acquisition means 121. For example, the adjustment means 124 can adjust the acquirable range of data and/or Information related to a user by designating data and/or Information related to a user, which is permitted to be acquired by the acquisition means 121.

Acquirable range of data and/or Information related to a user can be designated by, for example, the user. Adjustment means 124 can adjust the acquirable range of data and/or Information related to a user in response to an input by the user, whereby the user can provide or disclose, for example, only data and/or Information the user wishes to have reflected in the calculation of a score to the system 100.

The calculation means 122 can calculate a score in accordance with the acquirable range adjusted by the adjustment means 124. From the viewpoint of the system side, it is preferable that all available data and/or Information is disclosed by a user, because any available information can be used for the calculation of a score, which improves the precision of the score and in turn the precision of the determined product or service. However, from the viewpoint of the user side, there can be information that the user wishes to keep confidential. In this regard, the system 100 urges a user to disclose information by providing an incentive to the user in accordance with the acquirable range. As an exemplary incentive, the calculation means 122 can calculate a more favorable score for a user with a broader acquirable range of information. For example, the calculation means 122 can calculate a score in a manner that includes a feature of being honest to a score of a user with a broad acquirable range of information. In one example, the calculation means 122 can be configured to calculate a favorable score for a user who discloses information stored in a payroll card compared to a user who does not, as an incentive.

For example, the determination means 123 can determine a favorable product or service as a suitable product or service to a user having a favorable score calculated by the calculation means 122. Examples of favorable products r services include, but are not limited to, financial products with favorable transaction conditions, insurance products with favorable conditions for subscription, discounted travel plans, discounted consumer goods, etc.

Since the determined product or service that is suitable for a user would be more favorable for a broader acquirable range of information in this manner, the user can be urged to provide or disclose a broader range of information.

FIG. 6 shows an example of a configuration of a processing unit 120", which is an alternative embodiment of the processing unit 120.

The processing unit 120" has the same configuration as the processing unit 120, except in terms of comprising writing means 125. In FIG. 6, a constituent element that is identical to the configuration described above in reference to FIG. 3 is assigned with the same reference number, and descriptions thereof are omitted in this section.

The processing means 120" comprises acquisition means 121, calculation means 122, determination means 123, and writing means 125. The processing unit 120" may further comprise the adjustment means 124 described above by referring to FIG. 5.

The writing means 125 is configured to write a score calculated by the calculation means 122 into a token. For example, a token with a score written therein can be outputted from the processing unit 120" to an element external to the system 100 via the interface unit 110, whereby a calculated score can be utilized outside the system 100 via the token.

In this regard, the token is preferably a token whose owner is identified (i.e., identity verified or KYC (Know Your Customer)-ed token) because a KYC-ed token guarantees information stored in the token to be information on the person and can improve the credibility of the information. At this time, it is not necessary to disclose that a user is the owner of the token. Identity verification or KYC can be performed through zero-knowledge proof.

A token with a score written in may be, for example, provided to the determination means 123 and the score written in may be read out by the determination means 123.

In such a case, the calculation means 122 and the determination means 123 do not need to directly communicate. The score can be exchanged through the token.

The writing means 125 can be configured to write information indicating the product or service that is suitable for a user, which has been determined by the determination means 123, into a token. For example, a token with information indicating a product or service that is suitable for a user written therein can be outputted from the processing unit 120″ to an element external to the system 100 via the interface unit 110, whereby the information indicating the product or service that is suitable for the user can also be utilized outside the system 100 via the token. For example, a token that is KYC-ed guarantees information indicating a suitable product or service to be information on the owner of the token and can be utilized outside the of system 100 as credible information.

The aforementioned examples describe that the determination means 123 determines a product or service that is suitable for a user by utilizing a score calculated by the calculation means 122, but the system 100 may be configured to omit the determination means 123. Specifically, a score calculated by the calculation means 122 can be outputted from the processing unit 120 to an element external to the system 100 via the interface unit 110 in the system 100, whereby the calculated score can be utilized outside of the system 100 via a token. For example, a calculated score can be sold to a customer (e.g., financial institution, etc.) a insurance company, as subject of transaction.

In the examples shown in FIGS. 3, 5, and 6 described above, each constituent element of the processing unit 120 is provided within the same processing unit 120, but the present invention is not limited thereto. A configuration wherein each constituent element of the processing unit 120 is dispersed in a plurality of processing units is also within the scope of the invention. In such an embodiment, the plurality of processing units may be positioned within the same hardware part or positioned within near or remote but separate hardware parts.

Each constituent element of the system 100 described above may be comprised of a single hardware part or a plurality of hardware parts. If comprised of a plurality of hardware parts, each hardware part may be connected in any manner. Each hardware part may be connected via a wireless connection or a wired connection. The system 100 of the invention is not limited to a specific hardware configuration. The processing unit 120 comprised of an analog circuit instead of a digital circuit is also within the scope of the invention. The configuration of the system 100 of the invention is not limited to those described above, as long as the function thereof can be materialized.

3. Processing by a System for Determining a Product or Service that is Suitable for a User FIG. 7 shows an example of processing (processing 700) by the system 100 for determining a product or service that is suitable for a user. The processing 700 is performed in the processing unit 120 of the system 100. Processing 700 can also be performed in the processing unit 120′ and the processing unit 120″ in the same manner.

At step S701, the acquisition means 121 of the processing unit 120 acquires data and/or Information related to a user.

The acquisition means 121 may be configured to acquire data and/or Information related to a user, which is, for example, stored in the database unit 200 via the interface unit 110. Alternatively, the acquisition means 121 may be configured to acquire data and/or Information related to a user, which, for example, has been received from the user terminal apparatus 300 via the interface unit 110. Alternatively, the acquisition means 121 may be configured to acquire data and/or Information related to a user from, for example, a given place on a network. The acquisition means 121 can acquire data related to a user from, for example, a payroll card of the user (or a server managing a payroll card). The acquired data and/or Information related to a user is passed onto the calculation means 122.

At step S702, the calculation means 122 of the processing unit 120 calculates a score that multidimensionally represents a characteristic of a user based on the data and/or Information related to the user acquired at step S701.

For example, the calculation means 122 can calculate a score in accordance with a degree of correlation of data and/or Information related to a user with a parameter used for the calculation of the score. For example, the calculation means 122 determines the degree of correlation of data and/or Information related to a user with a concept related to a parameter used in the calculation of a score by referring to the database unit 200, which stores various pieces of information correlated with the concept related to the parameter used in the calculation of the score. Data and/or Information related to a user can comprise, for example, information related to "personality", "money", or "health".

For example, the calculation means 122 can determine the degree of correlation of data and/or Information related to a user with a concept related to "personality" and calculate a score in accordance with the determined degree of correlation. For example, the calculation means 122 can determine the degree of correlation of data and/or Information related to a user with a concept related to "money and calculate a score in accordance with the determined degree of correlation. For example, the calculation means 122 determine of can the degree correlation of data and/or Information related to a user with a concept related to "health" and calculate a score in accordance with the determined degree of correlation.

For example, the calculation means 122 can calculate a score that multidimensionally represents a characteristic of a user by utilizing a machine learning model that has learned the relationship between data and/or Information related to a plurality of users and a score. Data and/or Information related to a user can comprise, for example, information related to "personality", "money", or "health".

If, for example, the data and/or Information related to a user acquired at step S701 is inputted into a machine learning model, a score of the user can be outputted.

At step S703, the determination means 123 of the processing unit 120 determines a product or service that is suitable for a user by utilizing the score calculated at step S702. For example, the determination means 123 can determine a product or service corresponding to a feature contained in a score as a product or service that is suitable for a user. Alternatively, the determination means 123 can deduce a specific feature from a score and determine a product or service based on the deduced feature.

At step S703, the determination means 123 can deduce a specific feature from a score through any approach. In one example, the determination means 123 can extract a specific feature from features contained in a score. In another example, the determination means 123 can deduce a specific feature by applying a specific function for a score or a feature contained in a score.

A feature extracted from a score can be changed in accordance with the field of the determined product or service. For example, the determination means 123 can extract a specific feature in accordance with the field of the determined product or service from a feature contained in a score. For example, the determination means 123 can deduce a specific feature by applying a specific function in accordance with the field of the determined product or service for a score or a feature contained in a score. The system 100 can determine a product or service that is suitable for a user for a specific product or service by tuning a feature deduced from a score for the field of the specific product or service.

In this manner, a product or service that is suitable for a user is determined by utilizing a digital twin of the user in the processing 700. The precision of the determined product or service that is suitable for a user is further improved with higher precision of a digital twin of the user.

A product or service that is suitable for a user determined by the processing 700 can be utilized in any application. For example, the determined product or service that is suitable for a user can be presented to the user. Alternatively, the determined product or service that is suitable for a user can be written into a token of the user. Alternatively, the determined product or service that is suitable for a user can be utilized to develop another new product or service.

In the example described above in reference to FIG. 7, processing was described to be performed in a specific order, but the order of each processing is not limited to the described order. Processing can be theoretically performed in any order.

In the example described above in reference to FIG. 7, processing in each step shown in FIG. 7 was described to be materialized by the processing unit 120 and a program stored in the memory unit 130, but the present invention is not limited thereto. At least one of the processing in each step shown in FIG. 7 may be materialized by a hardware configuration such as a control circuit.

The example described above is an example in which the system 100 is a computer (e.g., server) installed at a service provider providing a service for determining a product or service that is suitable for a user, but the present invention is not limited thereto. The system 100 can be any information processing apparatus comprising a processing unit.

The present invention is not limited to the embodiments described above. It is understood that the scope of the present invention should be interpreted based solely on the claims. It is understood that an equivalent scope can be practiced by those skilled in the art based on the descriptions of the present invention and common general knowledge from the specific descriptions in the preferred embodiments of the invention.

INDUSTRIAL APPLICABILITY

The present invention is useful for providing a system, etc., which can determine a product or service that is suitable for a user with high precision by utilizing a score that multidimensionally represents a characteristic of a user, i.e., digital twin of the user.

REFERENCE SIGNS LIST

100 system
200 database unit
300 user apparatus
400 network

The invention claimed is:

1. A system for determining a product or service that is suitable for a user, the system comprising a processor, the system being connected to a user terminal apparatus and a dispersed network, the user terminal apparatus and the dispersed network storing data and/or Information related to a user, the processor being configured to:

communicate with the user terminal apparatus and the dispersed network to acquire data and/or Information related to the user;

calculate a score that multidimensionally represents a characteristic of the user by inputting the acquired data and/or Information related to the user into a machine learning model, the machine learning model having learned a relationship between data and/or Information related to a plurality of users with a score; and determine the product or service that is suitable for the user by utilizing the score, the determining comprising:

deducing a feature in accordance with a field of the product or the service from the score; and determining the product or the service associated with the feature, wherein the processor is further configured to:

adjust an acquirable range of the data and/or Information related to the user, in response to an input by the user, and calculate the score such that the broader the acquirable range is, the more favorable the score becomes.

2. The system of claim 1, wherein the determination means performs:

deducing a feature in accordance with a field of the product or the service from the score; and determining the product or the service based on the feature.

3. The system of claim 2, wherein the system is a system for determining a financial product that is suitable for a user, and the feature comprises a feature that can be used to evaluate a risk for the user.

4. The system of claim 3, wherein the system is a system for determining an insurance product that is suitable for a user, and the feature comprises a feature that can be used to evaluate a health and/or financial risk for the user.

5. The system of claim 2, wherein the system is a system for determining a travel plan that is suitable for a user, and the feature comprises a feature that can be used to evaluate a behavioral character of the user.

6. The system of claim 2, wherein the system is a system for determining a consumable good that is suitable for a user, and the feature comprises a feature that can be used to evaluate a preference of the user.

7. The system of claim 1, wherein the score comprises a feature that can be used to evaluate whether the user is a person who is trustworthy.

8. The system of claim 7, wherein the score comprises a feature related to personality, a feature related to money, and a feature related to health.

9. The system of claim 1, wherein the processor is configured to calculate the score in accordance with a degree of correlation of the acquired data and/or Information related to the user with at least one of a concept related to personality, a concept related to money, and a concept related to health.

10. The system of claim 1, wherein the data and/or Information comprises information stored in a payroll card.

11. The system of claim 1, wherein the processor is configured to write the score into a token the user owns, and
the processor is configured to be able to read out the score from the token.

12. The system of claim 11, wherein the processor is further configured to write information indicating the determined product or service into the token.

13. The system of claim 1, wherein the processor is configured to present the determined product or service to the user.

14. A method for determining a product or service that is suitable for a user, the method being performed by a system connected to a user terminal apparatus and a dispersed network, the user terminal apparatus and the dispersed network storing data and/or Information related to a user, comprising:

communicating with the user terminal apparatus and the dispersed network to acquire data and/or Information related to a user;
calculating a score that multidimensionally represents a characteristic of the user by inputting the acquired data and/or Information related to the user into a machine learning model, the machine learning model having learned a relationship between data and/or Information related to a plurality of users with a score; and
determining the product or service that is suitable for the user by utilizing the score, the determining comprising:
deducing a feature in accordance with a field of the product or the service from the score; and
determining the product or the service associated with the feature,
wherein the method further comprises:
adjusting an acquirable range of the data and/or Information related to the user, in response to an input by the user; and calculating the score such that the broader the acquirable range is, the more favorable the score becomes.

15. A non-transitory computer readable storage medium storing a program for determining a product or service that is suitable for a user, the program being executed in a computer system comprising a processor, the computer system being connected to a user terminal apparatus and a dispersed network, the user terminal apparatus and the dispersed network storing data and/or Information related to a user, the program causing the processor to perform processing comprising:

communicating with the user terminal apparatus and the dispersed network to acquire data and/or Information related to a user;
calculating a score that multidimensionally represents a characteristic of the user by inputting the acquired data and/or Information related to the user into a machine learning model, the machine learning model having learned a relationship between data and/or Information related to a plurality of users with a score; and
determining the product or service that is suitable for the user by utilizing the score, the determining comprising:
deducing a feature in accordance with a field of the product or the service from the score; and
determining the product or the service associated with the feature,
wherein the processing further comprises:
adjusting an acquirable range of the data and/or Information related to the user, in response to an input by the user; and
calculating the score such that the broader the acquirable range is, the more favorable the score becomes.

* * * * *